(12) United States Patent
Yang et al.

(10) Patent No.: US 8,440,453 B2
(45) Date of Patent: May 14, 2013

(54) FUNCTIONALIZATION OF NANOFLUIDIC CHANNELS

(75) Inventors: Peidong Yang, El Cerrito, CA (US); Rohit Karnik, Cambridge, MA (US); Kenneth Castelino, Berkeley, CA (US); Rong Fan, Pasadena, CA (US); Arun Majumdar, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 1533 days.

(21) Appl. No.: 11/969,010

(22) Filed: Jan. 3, 2008

(65) Prior Publication Data
US 2012/0171778 A1  Jul. 5, 2012

Related U.S. Application Data

(63) Continuation of application No. PCT/US2006/026318, filed on Jul. 6, 2006.

(60) Provisional application No. 60/697,332, filed on Jul. 6, 2005.

(51) Int. Cl.
*C12M 3/00* (2006.01)

(52) U.S. Cl.
USPC .................................................. 435/287.1

(58) Field of Classification Search .................. None
See application file for complete search history.

(56) References Cited

U.S. PATENT DOCUMENTS

| 7,077,939 | B1 | 7/2006 | Crooks et al. |
| 2003/0127329 | A1 | 7/2003 | DeVoe et al. |
| 2004/0235016 | A1 | 11/2004 | Hamers et al. |
| 2004/0262636 | A1 | 12/2004 | Yang et al. |
| 2008/0318245 | A1 * | 12/2008 | Smirnov ........................ 435/7.1 |

OTHER PUBLICATIONS

Merkoci et al., New materials for electrochemical sensing VI: carbon nanotubes, 2005, Trends in Anal Chem, 24(9): pp. 826-838.*
Fan, Rong et al. "Polarity Switching and Transient Responses in Single Nanotube Nanofludic Transistors", Physical Review Letters, Aug. 2005, vol. 95, Issue 8, ID 086607.
Fan, Rong et al. "DNA Translocation in Inorganic Nanotubes", Nano Letters, vol. 5, No. 9, pp. 1663-1667 (2005).
Karnik, Rohit et al. "Effects of Biological Reactions and Modifications on Conductance of Nanofluidic Channels", Nano Letters, vol. 5, No. 9, pp. 1638-1642 (2005).
Ito et al.—"Observation of DNA transport through a single carbon nanotube channel"—Chem. Commun., vol. 13, 2003, pp. 1482-1483.
Sun et al.—"Single Carbon Nanotube Membranes: A Well-Defined Model for Studying Mass Transport"—Journ. American Chem. Soc., vol. 122, No. 49, 2000, pp. 12340-12345.

* cited by examiner

*Primary Examiner* — N. C. Yang
(74) *Attorney, Agent, or Firm* — John P. O'Banion

(57) ABSTRACT

A functionalized nanofluidic channel and method for functionalization that provides control over the ionic environment and geometry of the nanofluidic channel with the immobilization of biomolecules on the inner surface of the channel and use of high ionic concentration solutions. In one embodiment, the surface charge of the nanochannel is controlled with the immobilization of a protein such as streptavidin in the nanochannel. In another embodiment, the biomolecules are receptors and changes in nanochannel conductance indicates ligand binding events. The functionalized nanofluidic channel can be easily adapted for use with microchannel arrays.

9 Claims, 6 Drawing Sheets

FUNCTIONALIZATION OF NANOFLUIDIC CHANNELS

CROSS-REFERENCE TO RELATED APPLICATIONS

This application claims priority from, and is a 35 U.S.C. §111(a) continuation of, co-pending PCT international application serial number PCT/US2006/026318, filed on Jul. 6, 2006, incorporated herein by reference in its entirety, which claims priority to U.S. provisional application Ser. No. 60/697,332 filed on Jul. 6, 2005, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to fluidic nanotube devices, and more particularly, to functionalized nanochannels providing modifiable channel geometry and ionic environment and devices fabricated therefrom.

2. Description of Related Art

The detection and analysis of interactions between biological molecules is a significant area of research in the healthcare and biotechnology fields. Many molecular detection, analysis and separation techniques have been developed and validated in recent years. For most processes, efficiency is a result of a trade-off between sensitivity, specificity, ease of operation, cost, speed and avoidance of false positives. Typical biological sensing techniques require a series of preparation steps, a number of reagents and schemes to separate components, a relatively large sample size and complex data analysis.

Miniaturization and mechanization of biological sensing techniques can lower sample sizes, reduce the time and expense of the process and increase diagnostic sensitivity. Emerging micro- and nano-technologies can decrease the size, weight and cost of sensors and sensor arrays by orders of magnitude, and increase their spatial and temporal resolution and accuracy. Novel functional materials such as quantum dots, photonic crystals, nanowires, carbon nanotubes, porous membranes, porous silicon and sol-gel matrices incorporating biomolecules have been used as sensing elements with various possible detection mechanisms.

Hollow inorganic nanotubes are of particular interest due to their potential applications in bioanalysis and catalysis. For example, silica nanotubes are of special interest because of their hydrophilic nature, easy colloidal suspension formation, and surface functionalization accessibility for both inner and outer walls. Such modified silica nanotubes and nanotube membrane have shown potential applications for bioseparation and biocatalysis.

In addition, one-dimensional nanostructures (nanotubes and nanowires) have also made miniaturized chemical and biological sensing elements possible. The ultrahigh surface to volume ratios of these structures make their electrical properties extremely sensitive to surface-adsorbed species, as has been shown with carbon nanotubes, functionalized silicon nanowires and metal nanowires Chemical and biological nanosensors are advantageous because of their potential for detecting very low concentrations of biomolecules or pollutants on platforms small enough to be used in vivo or on a microchip. For example, a room temperature photochemical $NO_2$ sensor has been demonstrated based on individual single-crystalline oxide nanowires and nanoribbons.

Chemical/sensing systems have also been developed using silica tubular membranes creating a new class of molecular sieves for molecular separation and electrochemical sensing based on the size of the molecules as well as interaction of the molecules with the surface functional groups of the tube. Normally, an inorganic nanotube membrane (polycarbonate or porous alumina) is set up to separate two salt solutions and a constant transmembrane potential is applied, then the transmembrane current is measured. When an analyte of comparable dimensions to the tube diameter is added to one of the solutions, a decrease in transmembrane current is sensed because of the current blocking by the molecules. Using such schemes, very small traces of different ions and molecules can be detected. These experiments, however, have all relied on using entire membranes as sensing elements. No significant efforts have been placed on single tube sensing, although the use of single nanotube sensing would obviously represent the miniaturization limit.

Nanofluidic channels and nanopores having dimensions comparable to the size of biological macromolecules such as proteins and DNA are important in applications such as single molecule detection, analysis, separation, and control of biomolecules. Previous work on nanopore or nanotube based single molecule detection can be broadly classified into two categories, namely: (i) non-functionalized nanopores; (ii) functionalized nanopores. Almost all of the prior work has involved the transmembrane protein ion channel α-Hemolysin (αHL) embedded in a suspended membrane separating two chambers filled with ionic solution. The entrance on the top (cis) side is about 2.6 nm in diameter whereas the narrow channel through the membrane that is closer to the bottom end (trans) is 1.4 nm in diameter. When a voltage bias of 120 mV is applied across the ion channel, an ionic current of about 120 pA is produced for ionic concentrations of 1 MKCl (the resistance is approximately $10^9 \Omega$). However, biological nanopores such as α-hemolysin offer single molecule sensitivity but are labile and difficult to handle.

However, inorganic channels on solid state chips have advantages over organic channels including providing better control over channel geometry, increased mechanical, electrical, thermal and chemical stability and are more amenable to integration into functional systems.

Therefore, a need exists for nanofluidic devices and nanotube structures which can be readily implemented, such as within fluidic sensing applications. The present invention fulfills those needs and others, while overcoming the drawbacks inherent in prior nanodevice and nanostructure approaches.

BRIEF SUMMARY OF THE INVENTION

The present invention pertains to fluidic nanotubes and devices fabricated from functionalized fluidic nanotubes. The fabrication of oriented, robust nanotube arrays is of use in nanoscale fluidic bioseparation, sensing, catalysis, and the like. The apparatus and methods of the present invention can be adapted to many different detection, separation and analytical applications and nanofluidic contexts. Although specific examples are used as illustrations, it will be understood that the apparatus and methods will be useful for any scheme that would benefit from intentional manipulation of ionic or electrostatic conditions within a nanochannel or nanochannel geometry.

Electronic detection of biomolecules with nanofluidic channels and nanopores having dimensions comparable to the size of biological macromolecules can serve as a highly selective and sensitive sensor that is compatible with current "lab-on-a-chip" micro-total-analysis systems. Miniaturized sensors or bioassays have three fundamental components: 1) a transport system for loading a sample and flushing fluid; 2) a sensing unit that produces a measurable signal or indicator in the presence of the molecule, and 3) a functionalized element that is part of the sensing unit configured to interact with an analyte.

The fluid transport system is generally connected to at least one nanotube with a nano-scale central channel. Flow through the nanochannel may be passive or may be active with the assistance of electroosmotic forces with the use of electrodes and may also include a means for controlling the flow of fluid and ions through the channels, such as a set of gate electrodes.

The sensing unit includes a means for determining conduction along the nanotube. Optionally, the sensing unit may also have an optical sensor used in combination to provide potential detection of labeled analytes.

The sensor preferably comprises a nanotube with a central channel that is functionalized with a plurality of biomolecules. The biomolecule may be a receptor or ligand, globular protein or some other molecule that will interact with an analyte of interest. The biomolecule may also serve to change the geometry, analyte flow rate or regulate ionic conditions within the nanochannel.

Another class of devices fabricated from fluidic nanotubes includes a nanofluidic transistor formed from a semiconductor nanotube and having source and drain connections, and optional gate electrode along the length of the nanotube. By way of example, another class of devices fabricated from fluidic nanotubes, which have been functionalized, comprises electrophoretic devices formed from insulating or semiconducting nanotubes, and having source and drain electrodes within the reservoirs proximal to each open end of the nanotubes. From these classes of fluidic devices, separately or in combination, numerous fluidic devices can be implemented, which include but are not limited to, nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, transistors, sensors, thermoelectric devices, photonic devices, nanoelectromechanical actuators, nanoelectromechanical sensors, and imaging devices. It will be appreciated that the devices described herein are based on the use of fluidic nanotubes in general; that is, their fabrication need not be based on a specific composition of nanotube but on the use of a fluidic nanotube.

The ability to spacially and temporally tune the ionic and electrostatic environment within a nanotube channel will allow the manipulation of small quantities of charged biomolecules for biological analyses on solid state chips. The capability of ionic environmental control can be integrated into existing microfluidic and nanofluidic circuits and schemes.

According to one aspect of the invention, a nano-scale detector is provided with a non-organic nanotube with a channel functionalized with a biomolecule and a means for detecting conductance of the nanotube.

According to another aspect of the invention, a functionalized fluidic nanotube is provided with a tubular member having first and second ends, and an inner bore between said first and second ends having a diameter of approximately 100 nanometers or less with a non-porous inner wall. A layer of biomolecules forming a lining on the inner wall of the tubular member; and means for measuring conductance of the tubular member.

Another aspect of the invention also provides a means for varying the concentration of ions in a fluid presented to the inner bore of the tubular member and a means for creating an electric field within the tubular member.

A further aspect of the invention is to provide a functional component of a device selected from the group of devices consisting essentially of nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, transistors, sensors, thermoelectric devices, photonic devices, nanoelectromechanical actuators, nanoelectromechanical sensors, nanoscale fluidic bioseparators, and imaging devices.

According to another aspect of the invention a method of controlling the geometry of a nanofluidic channel is provided comprising immobilizing biomolecules in a nanofluidic channel and exposing said biomolecules to a solution with a high concentration of ions.

A method of detecting the presence of a binding events between biomolecules is also provided, comprising the steps of immobilizing a plurality of first biomolecules on nanochannel surface and measuring nanochannel conductance, exposing said immobilized biomolecules to an ionic solution containing a second biomolecule and measuring the conductance of said nanochannel a second time and then comparing said first conductance measurement and said second conductance measurement to determine a change in conductance. The conductance measurements can also be taken in the presence of low and high ion concentration solutions and compared.

An aspect of the invention is a method of controlling conductance characteristics of a nanofluidic channel (nanochannel), comprising immobilizing biomolecules in said channel. In one embodiment, the biomolecules comprise streptavidin. In one mode, the biomolecules modify surface charge. In another mode, the biomolecules occlude a portion of said nanochannel. In a further mode, the biomolecules alter nanochannel geometry. In another mode, immobilization of streptavidin in the nanochannel modifies surface charge and nanochannel geometry.

Another aspect of the invention is a method of controlling surface charge and device geometry in a nanofluidic channel (nanochannel) comprising immobilizing streptavidin in the nanochannel.

Another aspect of the invention is a method of sensing surface charge in a nanochannel, comprising measuring nanochannel conductance.

Another aspect of the invention is a method of detecting presence of biomolecules immobilized on nanochannel surfaces, comprising measuring nanochannel conductance.

Another aspect of the invention is a method of sensing surface charge and the presence of biomolecules immobilized on nanochannel surfaces in both surface charge-governed and geometry-governed regimes, comprising measuring nanochannel conductance.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 5. It will be appreciated that the apparatus may vary as to configuration and as to details of the parts, and that the method may vary as to the specific steps and sequence, without departing from the basic concepts as disclosed herein.

Figure 1:
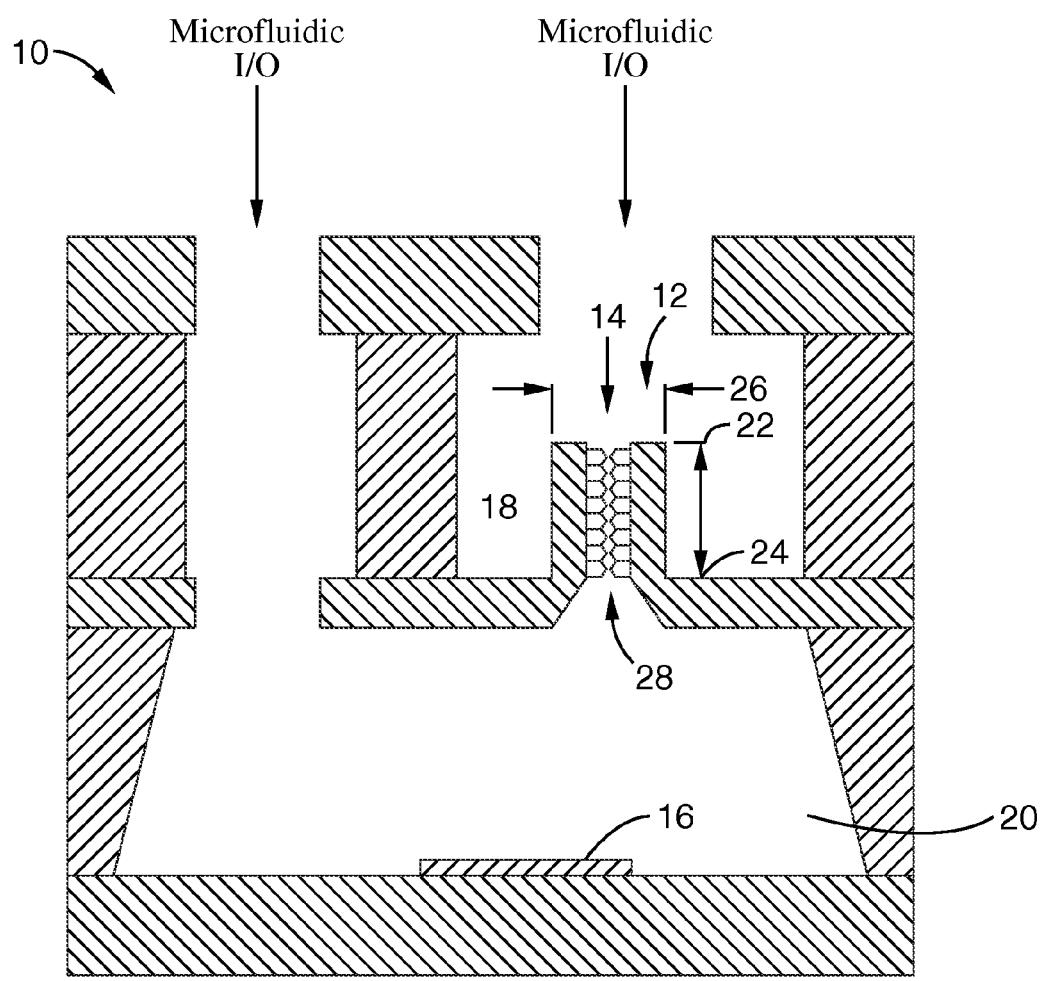
FIG. 1 is a schematic of a microfluidic system with a nanochannel according to the present invention.

Referring first to FIG. 1, a schematic of one embodiment of a nanofluidic device 10 with at least one nanotube 12 with a channel 14 and a means 16 for determining conduction of the nanotube 12 is shown. The schematic also shows a source reservoir 18 and a sink reservoir 20 interconnected by nanotube 12. Although reservoirs 18, 20 are shown, it will be understood that the reservoirs may also be microchannels or other fluid channel. The nanotube 12 may also be an etched channel and part of a plurality of nano-scale tubes that form an array of tubes or pores fluidly connected to a system of microchannels and reservoirs. Nanotubes in the array may be arranged in series or in parallel and may vary in length and diameter. A single nanotube 12 is used for illustration.

It will be appreciated that a central component of devices fabricated from fluidic nanotubes 12 are the nanotubes themselves. Nanotubes 12 can be fabricated according to various methods known in the art and have various compositions of matter. While fluidic devices can be made using carbon-based nanotubes, such nanotubes are generally hydrophobic and may be unsuitable for fluidic applications without modification and therefore non-carbon based nanotubes are preferred. It is also preferred that the non-carbon-based nanotube 12 be non-porous (e.g., having a seamless tube wall) for use in fluidic applications. The tubular nanotube 12 has a first end 22 and a second end 24 and a non-porous inner bore or channel 14 between said first and second ends. The inner channel 14 of nanotube 12 has a diameter 26 and an inner wall 28.

Fluid flow and chemical reactions that take place in nanometer scaled structures are fundamentally different than take place in larger scale channels, because the molecules involved are approximately equal to the dimensions of the nanotube in which the reactions occur. The unique properties of nanochannels arise when the nanochannel size is comparable to either of two length scales: (a) the range of electrostatic interactions in solution and (b) size of the analyte molecules. Since biomolecular analytes are typically charged and have sizes comparable to the above length scales, variable ionic conditions have a predictable effect on the transport characteristics of nanochannels in the presence of biomolecular charge and size of the analyte.

It has been shown that a solid surface such as inner wall 28 in contact with an ionic solution is often charged due the presence of ionized surface groups or adsorbed ions. Counterions in solution accumulate near this charged surface and co-ions are repelled, shielding the surface charge in a characteristic distance known as the Debye length. The Debye length, $l_D$, characterizes the distance of ionic interactions in solution and can be made to span the range $1\,nm \leq l_D \leq 100\,nm$ by adjusting the ionic concentration of the buffer solution. Accordingly, in microchannels, the Debye length is usually much smaller than the channel dimensions and the bulk of the solution is shielded from the surface charge. When the channel size is smaller than the Debye length and the nanochannel surface is charged, the channel becomes a unipolar solution of counterions at a concentration that neutralizes the surface charge. The co-ions are essentially repelled from the channel. It is therefore possible to create conditions in nanotube 12 where the electrical double layer confined to the inner wall 28 or ranging out into the channel 14.

Within the Debye layer, the surface charge controls ionic concentrations, which in turn affect the nanochannel conductance that can be calculated for a given surface charge or potential. When a 1:1 electrolyte at a bulk concentration of n molecules/m is introduced in a nanochannel of height 2 h and surface charge σ, the conductance deviates significantly from that of bulk electrolyte when σ/eh is comparable to n; that is, when the effective concentration of ions required to neutralize the surface charge, σ/eh, is comparable to bulk ion concentration, n, surface charge plays an important role.

In the regime of low electrolyte concentration, σ/eh>>n, surface charge governs the ionic concentration inside the channel to maintain electroneutrality ($n_\pm$=σ/eh), which in turn controls the nanochannel conductance. Generally less than 1M ionic solutions are within the low regime. Thus the nanochannel conductance (G) for a 1:1 electrolyte, neglecting electroosmotic effects is given by the equation:

$$G = 2\sigma \frac{\mu_{+/-} w}{l}$$

In this equation, the symbol μ is ionic mobility (subscripts denote cation/anion) and w and l are the channel width and length, respectively. Hence, any functionalization of nanochannel surfaces with different surface groups and biomolecules can be expected to change surface charge and the nanochannel conductance. A signature of this regime is that conductance becomes independent of bulk ionic concentration as well as the channel height.

In the high concentration regime, σ/eh, n and conductance becomes largely independent of surface charge. In this regime, conductance depends on channel height and increases linearly with ionic concentration, as shown by the following equation:

$$G = 2neh\frac{(\mu_+ + \mu_-)w}{l}$$

If the size of the biomolecules in the channel is comparable to the channel size, the resulting change in channel geometry (h) would result in a change in nanochannel conductance.

Consider a biomolecule with charge q and volume V present in a solution with ionic concentration n in the nanochannel. The number of charges on the biomolecule is qle, where e is the charge of an electron. The number of conducting ions introduced due to biomolecule charge is expected to be of the order of qle, while the number of excluded ions is of the order of nV. These contributions are analogous to the equations described above with the first contribution depending only on charge and the second one varying with geometry and ionic concentration. The biomolecule charge effect dominates at lower ionic concentration, but as the ionic concentration increases, the number of ions displaced due to the biomolecule volume increases. This exactly offsets the effect of biomolecule charge at a certain concentration, i.e., when n~qleV. At higher concentrations, the volume exclusion effect dominates.

Hence, in both the high and low concentration schemes, measurement of electrical conductance of nanochannels offers means of probing biological reactions and modifications on surfaces. In the past, electrokinetic measurements in microslits have been used for the characterization of surfaces and measurement of protein adsorption. However, electrokinetic characterization is often cumbersome, involving the application of pressure and the measurement of flow rates. In nanochannels, surface effects dominate and we can expect biological modifications and reactions to be detected directly by simply measuring the conductance.

It can be seen that the surface of inner wall 28 of nanotube 12 can be functionalized with immobilized biomolecules, for example, and detect conductance changes and control the ionic and structural conditions of the channel 14 of the nanotube 12. Functionalization of the surfaces 28 could enable the detection of specific interactions and selective binding to target biomolecules with a very low sample size, even approaching single protein. Likewise, surface functionalization will allow charge sensitive biosensing and label free detection of binding events.

Immobilized biomolecules can also selectively alter the geometry of the nanochannel as well as allow the manipulation and selection of nanochannel environment for passive transport, segregation or sizing of ionic or molecular species through an array of nanochannels.

The electrical properties of the nanotubes are highly sensitive to surface charge transfer and changes in the surrounding environment. Accordingly, functionalization of the inner wall 28 may be accomplished with a wide variety of biomolecules and can be specifically tailored to a desired diagnostic procedure, assay or molecule. Such biomolecules may be receptors, ligands, peptides, oligonucleotides or may be inorganic.

Accordingly, nanochannel conductance can be used to sense surface charge and the presence of biomolecules immobilized on nanochannel surfaces in both surface-charge-governed and geometry-governed regimes. The devices provide for an integrated nanofluidic platform with a robust electronic probing scheme that is amenable to scaling and multiplexing. This technique is also useful for charge-sensitive biosensing, allowing label-free detection of binding of small molecules and kinase activity, which are difficult to detect conventionally.

Figure 2:
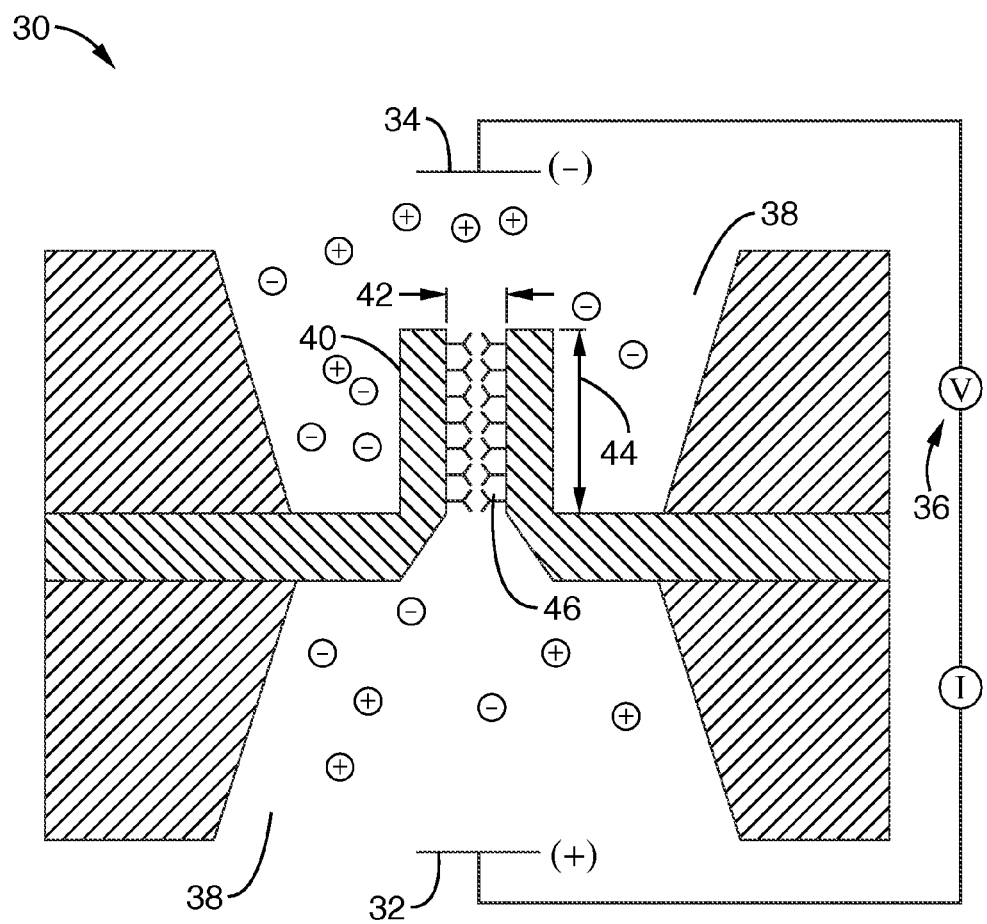
FIG. 2 is a schematic of a nanochannel according to another embodiment of the invention with electrodes providing electrical bias and generating ionic current.

In a second embodiment, shown schematically in FIG. 2, the apparatus 30 also includes at least one positive electrode 32 and at least one negative electrode 34 that are connected to a power source 36. Electrodes 32,34 are preferably placed on opposite sides of the nanofluidic channels 38 for applying electrical bias and generating ionic current. Nanochannel 38, preferably has at least one dimension 42,44 less than or equal to the Debye length so that electrostatic fields can penetrate throughout the channel enabling direct ionic or molecular manipulation using surface charge or field-effect in the nanotube 40.

In this embodiment, the ionic concentrations are both spatially and temporally controllable by electrostatic fields due to the microfabricated gate electrodes. By controlling the surface charge density in a region along the length of the channel, the ion current can be modulated, similar to modulation of charge transport in a field effect transistor due to a gate bias. This capability may be harnessed for applications such as isoelectric focusing of proteins and analyte stacking, while retaining the design flexibility of microfabrication and the controllability of gating voltage.

The functionalized channels 46 could be part of any of the following nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, sensors, thermoelectric devices, photonic devices, nanoelectromechanical actuators, nanoelectromechanical sensors, nanoscale fluidic bioseparators, imaging devices, and combinations thereof.

The invention may be better understood with reference to the accompanying examples, which are intended for purposes of illustration only and should not be construed as in any sense as limiting the scope of the present invention as defined in the claims appended hereto.

Example 1

Conductance characteristics of nanofluidic channels (nanochannels) that can be selectively manipulated generally fall into two categories: at low ionic concentrations, conductance is governed by surface charge while at high ionic concentrations it is determined by nanochannel geometry and bulk ionic concentration.

Aminosilane chemistry and streptavidin-biotin binding were used to study the effects of surface reactions on nanochannel conductance at different ionic concentrations. Immobilization of small molecules such as aminosilane or biotin mainly changes surface charge, affecting conductance only in the low concentration system. However, streptavidin not only modifies surface charge but also occludes part of the channel, resulting in observable conductance changes in both low and high concentration schemes.

In order to demonstrate the effect of biomolecules on microchannel conductance, a nanochannel device was constructed. Fabrication of the nanochannel device began with a 30 nm thick layer of polysilicon deposited on a fused silica wafer using a low-pressure chemical vapor deposition (LPCVD) process and then subsequently patterned, forming sacrificial material that defined the nanochannels. Polysilicon film thickness was measured using a Nanospec 3000 film analysis system (Nanometrics) as well as with an Alpha-Step IQ surface profiler (KLA-Tencor) after patterning the thin film. A 2 µm thick low-temperature oxide was then deposited in a LPCVD process, annealed, patterned, and etched down to access the nanochannel ends.

Microchannels with access holes were fabricated on another fused silica wafer. The nanochannel and microchannel components were then bonded together using a transfer bonding technique with poly-(dimethylsiloxane) (PDMS) (Sylgard 184, Dow Corning) as an adhesive.

A number of staggered nanochannels were used in the fabrication process such that only one set of nanochannels bridged the microchannels. After bonding, nanochannels were formed by etching the sacrificial polysilicon with xenon difluoride gas at a pressure of 3 Torr for 1.5 hours. Once the channels were formed, the entire device was treated with oxygen plasma at 300 W for 10 minutes in a plasma etcher (Technics).

The plasma-treated surfaces of the channels were immersed in a 2% solution of (3-aminopropyl)trimethoxysilane (APT-MS) (Gelest, Inc.) in ethanol for 1 hour at room temperature, followed by a 5-minute ethanol rinse. The devices were then immersed in a 0.1× phosphate-buffered saline (PBS, pH 7.2, Invitrogen; 10×PBS is an aqueous solution of 1.55 M NaCl, 0.015 M $KH_2PO_4$, and 0.027 M $Na_2HPO_4$). Biotinylation of the surface was done by treating the aminosilane-coated surface with a 10 mM solution of Sulfo-NHS-SS-Biotin (sulfosuccinimidyl 2-(biotinamido)-ethyl-1,3-dithiopropionate) (Pierce Biosciences) in 0.1×PBS for 1 hour at room temperature. Under these conditions, the succinimide moiety reacts readily with the primary amine group of the APTMS resulting in cross-linking biotin to the surface. The NHS-SS-biotin cross-linker was used because of its long spacer arm, which reduces steric constraints leading to better binding efficiency of avidins. Residual amine groups, if any, were then passivated by treating the surface with a 10 mM solution of n-hydroxy-succinimide (NHS) (Sigma Aldrich) in 0.1×PBS for 1 hour at room temperature. (1×PBS corresponds to an ionic concentration of 0.15 M).

Following each step of surface reactions, electrical conductance of the nanochannels was measured at a range of buffer concentrations using a Keithley 6430 sub-femtoamp source meter controlled through a GPIB interface by a real-time control and analysis MATLAB program. Ag/AgCl electrodes were used to make electrical contact with solutions through access holes at the ends of microchannels. While solutions were changed, conductance measurements and rinses were carried out alternately to ensure complete rinsing.

Figure 3A:
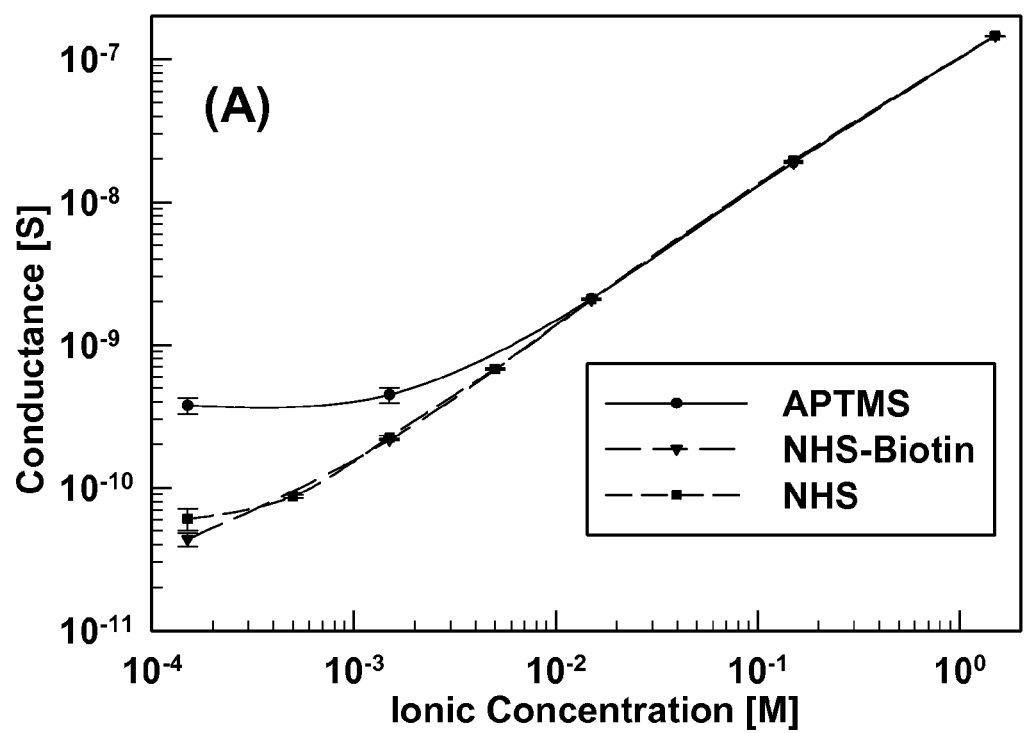
FIG. 3A is a plot of nanochannel conductance versus ionic concentration after various steps of surface functionalization.
Figure 3B:
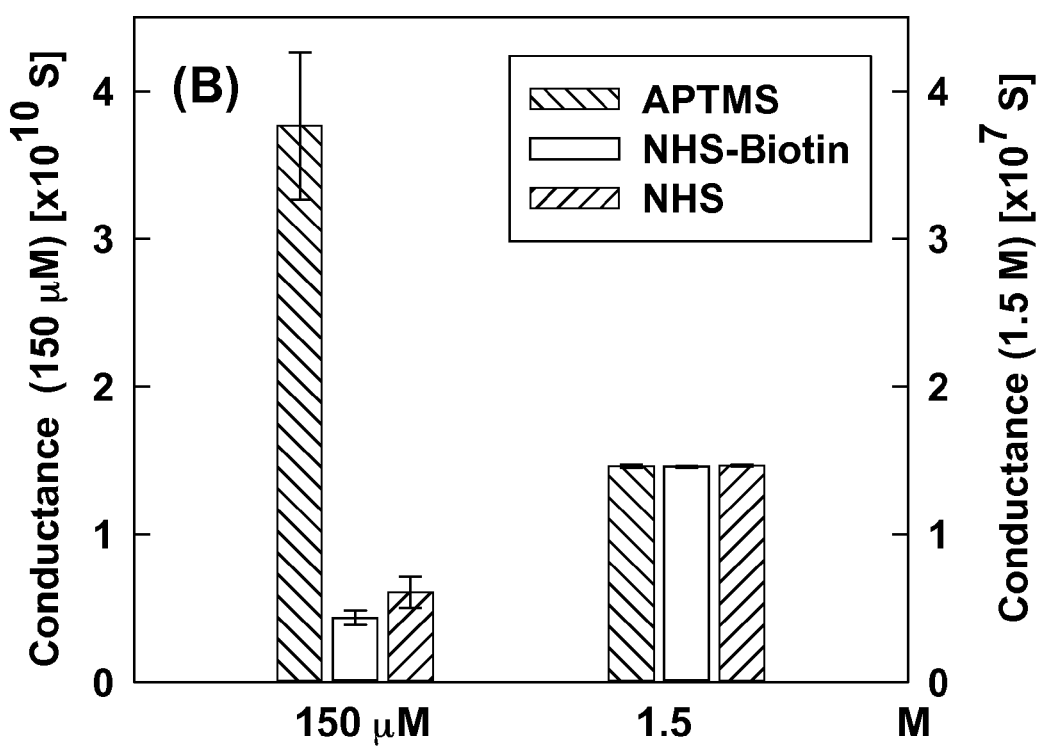
FIG. 3B is a detailed plot of conductance at the highest and lowest buffer concentrations.

Nanochannel conductance for a range of concentrations from 0.001× to 10×PBS after each step of surface modification was obtained. The microchannel device was first treated with APTMS, followed by NHS-SS-biotin and then NHS. Changes in nanochannel conductance after the various steps of surface functionalization of the channels at different buffer concentrations is shown in FIG. 3A and FIG. 3B. As seen in FIG. 3A, APTMS functionalization resulted in high conductance at low ionic concentrations. This conductance dropped to 11% of its original value upon treatment with NHS biotin. Subsequent treatment with NHS increased conductance slightly. No appreciable change in conductance was observed at high ionic concentrations indicating absence of steric blocking. FIG. 3B is a detailed plot of conductance at the highest and lowest buffer concentrations. The error bars correspond to five measurements at each point.

It was observed that at higher buffer concentrations, conductance varied linearly with concentration. Approximating 10×PBS as 1.55 M NaCl with an equivalent conductivity of $10^{-2}$ m²S/mol (or $\mu_+ + \mu_- = 10.4 \times 10^{-8}$ m²/V s)) and device geometry of 10 parallel 120 µm×3.5 µm×30 nm channels (first two dimensions estimated from micrographs), the expected conductance is calculated to be $1.35 \times 10^{-7}$ S, which is in reasonable agreement with the measured nanochannel conductance under the same conditions.

The conductance was repeatable from device to device, confirming the integrity of nanochannels and the microchannel interface. However, at low buffer concentrations, nanochannel conductance deviated significantly from linearity and was seen to level off for the APTMS treated nanochannels. At pH 7.2, the amino groups may be expected to be positively charged.

Assuming that the conducting ions are $Cl^-$ with a mobility of $7.9 \times 10^{-8}$ m²/(V s), the estimated surface charge is approximately 8 mC/m². In this case, σleh corresponds to about 5 mM, which is much larger than the bulk concentration of ~150 µM and hence σleh>>n. Treatment with NHS-SS-biotin drastically lowered conductance at low buffer concentrations, presumably due to reaction of the amino group with the NHS group resulting in a moiety with no charge. In this case, surface charge was lowered to such an extent that and σleh is comparable to n and the calculated predictions of conduction are not valid. However, since conductance decreases monotonically with bulk concentration, the equations put an upper bound of about 1 mC/m² on the surface charge.

Further treatment with NHS did not result in a large change in conductance. To clearly illustrate charge-governed and geometry-governed regimes, conductance values at 10 3× and 10×PBS (~150 µM and 1.5 M NaCl) for the three surfaces are shown in FIG. 3B. It can be seen that functionalization of nanochannel surfaces with small molecules resulted in a large change in surface charge, detected at low buffer concentrations, while conductance values at high buffer concentration remained unchanged, indicating no change in nanochannel geometry.

Example 2

To study the effect of biological binding reactions on nanochannel surfaces, 1 mg/mL Alexa Fluor 488 labeled streptavidin (Molecular Probes, Eugene, Oreg.) in 0.1×PBS was introduced into a test device configured as described in Example 1 for 10 hours at room temperature, followed by rinsing in buffer. To ensure that any observed changes were not due to effects external to nanochannels such as blocking of nanochannel inlets, another nonbiotinylated control device was prepared by treatment with APTMS followed by NHS and was similarly treated with streptavidin. Use of fluorescently labeled streptavidin enabled electrical measurement as well as direct optical confirmation of the presence or absence of streptavidin on nanochannel surfaces.

Figure 4A:
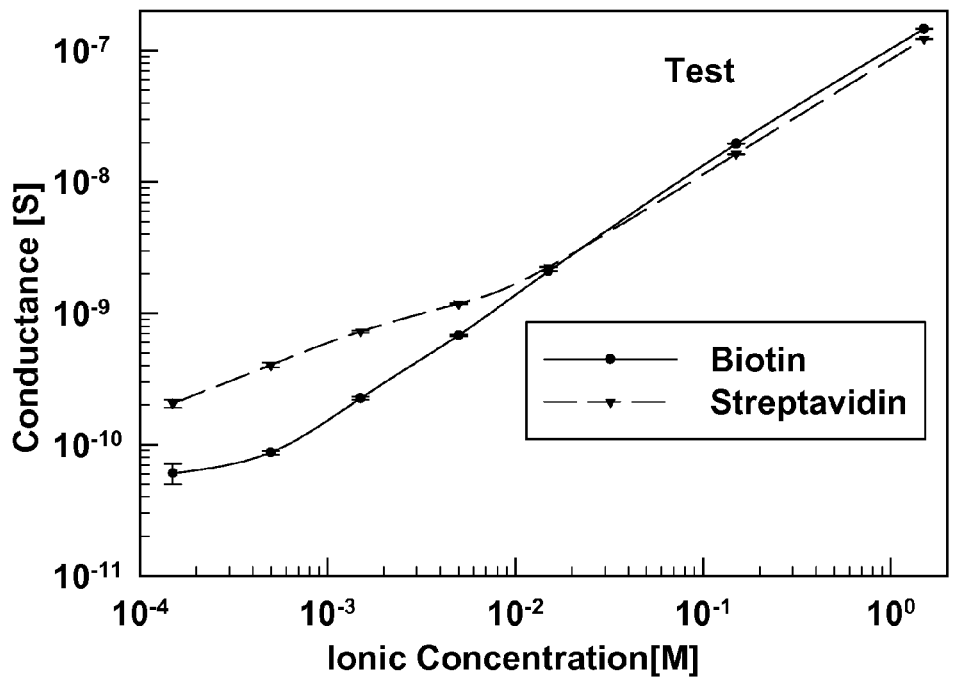
FIGS. 4A-4B are conductance measurements of the test device with a functionalized nanochannel and a control nanochannel over a range of ionic concentrations.
Figure 4B:
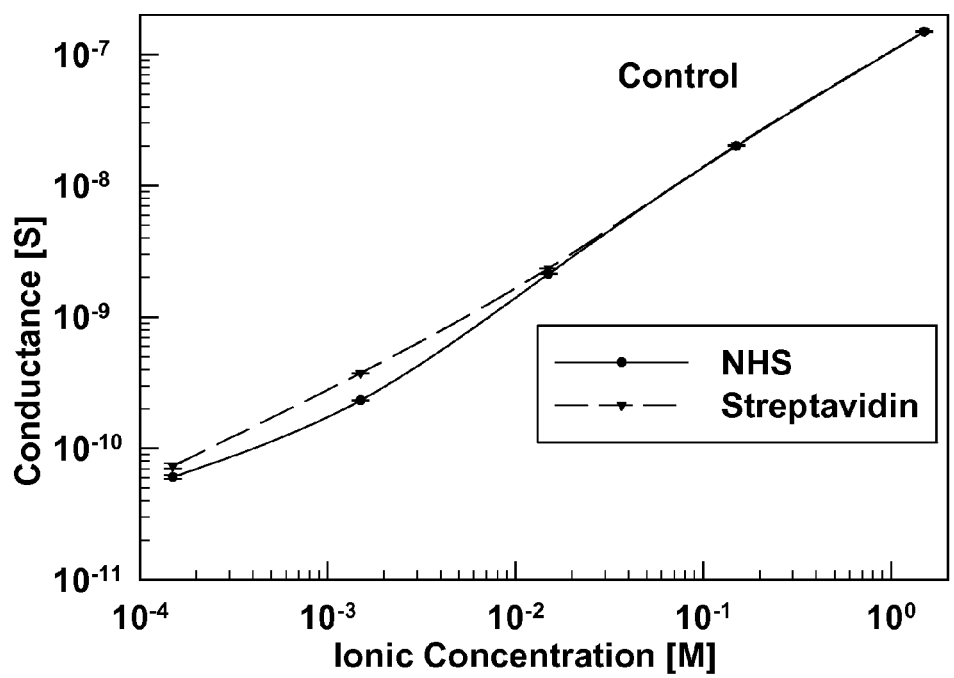

Referring now to FIGS. 4A and 4B, the conductance response of the test device functionalized with NHS-SS-biotin and passivated with NHS over a range of ionic concentrations is shown. The immobilized fluorescent streptavidin was imaged optically by fluorescence images obtained with a Nikon TE2000-U inverted epifluorescence microscope using an ORCA-ER (Hamamatsu Photonics Gmbh) camera to confirm the binding reaction. Referring also to FIG. 4B, conductance measurements for the control device passivated completely with NHS can be seen. No fluorescent signal was observed in this case indicating that streptavidin did not get immobilized on the surface (inset). PBS buffer was used for the measurements.

Accordingly, conductance measurements revealed large changes in conductance of the biotinylated nanochannels (test device) in FIG. 4A at both low and high ion concentrations, but little change in conductance of the nonbiotinylated nanochannels (control device) as seen in FIG. 4B. Further, this is corroborated by, which clearly showed immobilization of streptavidin in the test device but not in the control device.

Figure 5:
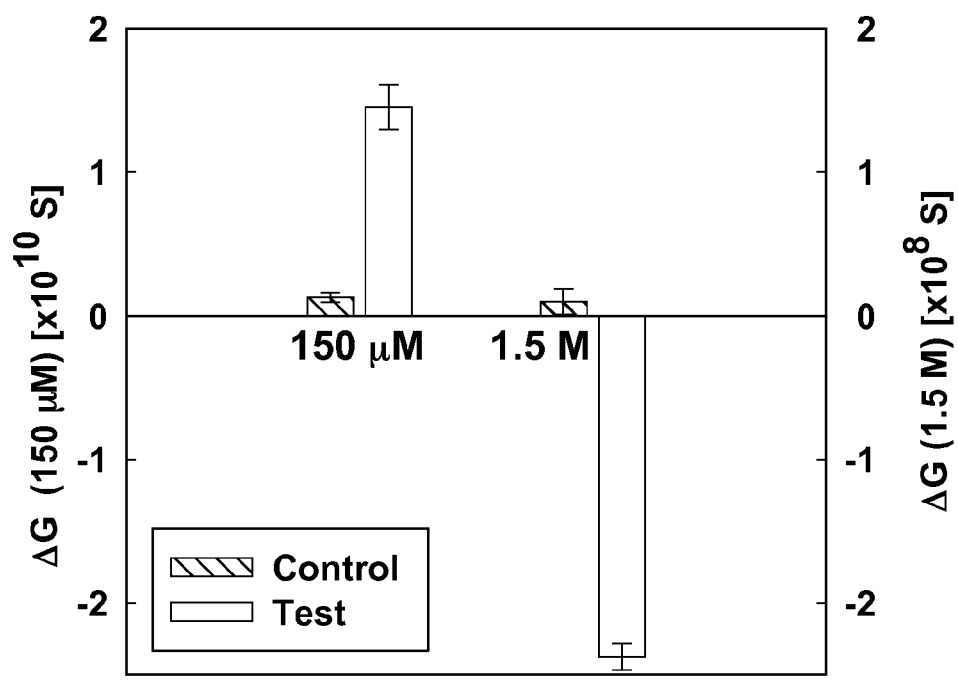
FIG. 5 is a graph showing changes in nanochannel conductance at low and high ionic concentrations according to an aspect of the present invention.

Conductance measurements in charge-governed and geometry-governed regimes shown in FIG. 5 reveal that immobilization of streptavidin in the nanochannels resulted in changing not only the surface charge but also the device geometry. At 10×PBS, conductance of the biotinylated nanochannels dropped by about 15% when streptavidin was introduced, indicating an effective reduction in channel size from about 30 to 25 nm or an immobilized layer effectively 2.5 nm thick on the surface. This change is consistent with the globular size of streptavidin (5-6 nm) and the change in size of colloids on protein binding reported in other studies. At low ion concentrations, conductance of the biotinylated nanochannels showed an increase, which implies an increase in the surface charge due to immobilization of streptavidin. Streptavidin with a mildly acidic pI of 5 is reported to have about two electron charges at pH 7.2, which qualitatively explains the increase in conductance. The conductance of the non-biotinylated nanochannels remained relatively unchanged, indicating that the changes observed in the test device can be attributed to the streptavidin binding reaction.

It can be seen that the biological binding events modulate surface charge and create a change in the nanochannel geometry. Moreover, conductance values were highly repeatable even after rinsing with different buffer concentrations. At the lowest buffer concentration, APTMS-treated surfaces showed the largest variability in conductance. This variability may be due to the presence of bivalent phosphate counterions in PBS, since multivalent ions are known to adsorb and sometimes even reverse charge on highly charged surfaces. In contrast, NHS and NHS-SS-biotin treated surfaces were extremely stable after rinsing with different buffer concentrations; conductance varied by less than $10^{-11}$ S in some cases. Assuming that change in conductance is roughly equivalent to a change in ionic concentration of $\Delta \sigma / eh$, it corresponds to variations in surface charge of approximately 0.1 mC/m² or one electron charge per 400 Å×400 Å area. This observation suggests that electrochemically stable nanochannel surfaces can be used as highly sensitive probes for measuring changes in surface charge. At high ionic concentrations, a variation of about 1% in nanochannel conductance was observed. This could be due to slight variations in concentration and temperature since the viscosity of water changes by 2% per 1° C. change in temperature in the 20-30° C. range, resulting in changes in ionic mobilities and conductance. Since the room temperature remained at 23±0.5° C. during the course of the experiment, these variations are not expected to materially affect the results. Another aspect of streptavidin immobilized on nanochannel surfaces is the deviation of conductance at low concentrations from that of nanochannels with a constant surface charge. This behavior could arise from a number of effects including charge regulation of streptavidin due to changes in pH, discreteness of charge, adsorption of ions, nonplanar geometry due to streptavidin, etc.

These experiments indicate that biomolecule charge and volume have opposite effects on nanochannel conductance: biomolecule charge increases the number of conducting ions in the nanochannel whereas volume exclusion of ions decreases the number of conducting ions. This is observed even when the nanochannel has a comparatively low surface charge to begin with, as in the present case. These experiments demonstrate that the ionic conductance of nanochannels reflects an interplay between the competing effects of biomolecule charge and size.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A functionalized fluidic nanotube, comprising:
   a tubular member having first and second ends, and an inner bore between said first and second ends having a diameter of approximately 100 nanometers or less;
   said tubular member having a non-porous inner wall;
   a layer of biomolecules forming a lining on said inner wall of said tubular member; and
   a sensor for measuring conductance of said tubular member.

2. A nanotube as recited in claim 1,
   wherein said layer of biomolecules is configured for varying the concentration of ions in a fluid presented to said inner bore of said tubular member.

3. A nanotube as recited in claim 1, wherein said biomolecule is a receptor capable of coupling with a ligand;
   wherein said conductance of said tubular member is changed after said ligand couples with said receptor.

4. A nanotube as recited in claim 1, wherein said biomolecule is a protein.

5. A nanotube as recited in claim 1, wherein said biomolecule is streptavidin.

6. A nanotube as recited in claim 1, wherein said layer of biomolecules occludes a portion of said inner bore of said tubular member in the presence of fluids with high ion concentrations.

7. A nanotube as recited in claim 1, wherein said layer of biomolecules modifies the ionic concentration to occlude a portion of said inner bore of said tubular member in the presence of fluids with high ion concentrations.

8. A nanotube as recited in claim 1, further comprising:
   one or more electrodes coupled to the tubular member for creating an electric field within said tubular member.

9. A nanotube as recited in claim 1, wherein said nanotube is a functional component of a device selected from the group of devices consisting essentially of nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, transistors, sensors, thermoelectric devices, photonic devices, nanoelectromechanical actuators, nanoelectromechanical sensors, nanoscale fluidic bioseparators, and imaging devices.

\* \* \* \* \*